United States Patent [19]

Fabre et al.

[11] 4,128,650
[45] Dec. 5, 1978

[54] DIBENZO[de, h]QUINOLINE DERIVATIVES

[75] Inventors: Jean-Louis Fabre, Paris; Daniel Farge, Thiais; Claude James, Paris, all of France

[73] Assignee: Rhone-Poulenc Industries, Paris, France

[21] Appl. No.: 798,139

[22] Filed: May 18, 1977

[30] Foreign Application Priority Data

May 21, 1976 [FR] France ................... 76 15379

[51] Int. Cl.² ................. A61K 31/47; C07D 215/20
[52] U.S. Cl. ........................... 424/258; 260/325 PH; 546/75; 546/71; 546/144
[58] Field of Search ............... 424/258; 260/287 P, 260/289 C

[56] References Cited

U.S. PATENT DOCUMENTS

| 2,086,704 | 7/1937 | Ebel | 260/289 C |
| 3,673,182 | 6/1972 | Brack | 260/289 C |
| 3,673,189 | 6/1972 | Curran et al. | 260/289 C |
| 3,717,643 | 2/1973 | Archer | 260/289 C |

Primary Examiner—Donald G. Daus
Assistant Examiner—David E. Wheeler
Attorney, Agent, or Firm—Stevens, Davis, Miller & Mosher

[57] ABSTRACT

Compounds of the formula:

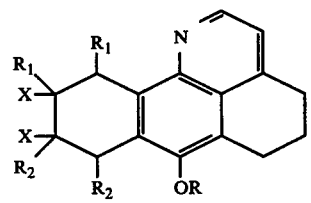

wherein the symbols X each represent hydrogen or methoxy, R represents hydrogen or carboxymethyl, the symbols $R_1$ each represent hydrogen or together represent a valency bond and the symbols $R_2$ each represent hydrogen or together represent a valency bond, the pair of symbols $R_2$ having the same significance as the pair of symbols $R_1$, and when the symbols $R_1$ and $R_2$ represent hydrogen the symbol X also represents hydrogen, are new compounds possessing antiviral activity.

8 Claims, No Drawings

DIBENZO[de,h]QUINOLINE DERIVATIVES

This invention relates to new therapeutically useful dibenzo[de,h]quinoline derivatives, processes for their preparation and pharmaceutical compositions containing them.

The new dibenzo[de,h]quinoline derivatives of the present invention are those of the general formula:

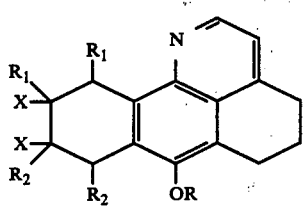

wherein the symbols X each represent a hydrogen atom or a methoxy radical, R represents a hydrogen atom or a carboxymethyl radical (i.e.—CH$_2$COOH), the symbols R$_1$ each represent a hydrogen atom or together represent a valency bond and the symbols R$_2$ ach represent a hydrogen atom or together represent a valency bond, the pair of symbols R$_2$ having the same significance as the pair of symbols R$_1$, and when the symbols R$_1$ and R$_2$ represent hydrogen atoms, the symbol X also represents a hydrogen atom, and pharmaceutically acceptable salts of those compounds wherein R represents a carboxymethyl radical, for example alkali metal, alkaline earth metal, ammonium and amine salts.

According to a feature of the invention, the compounds of general formula I, wherein R represents a hydrogen atom and X, R$_1$ and R$_2$ are as hereinbefore defined, are prepared by the process which comprises the partial catalytic hydrogenation of a compound of the general formula:

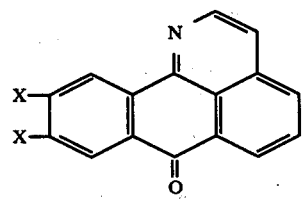

wherein the symbols X have the appropriate significances as hereinbefore defined.

The reaction is generally effected in the presence of a hydrogenation catalyst, preferably Adams platinum, either at a temperature between 20° and 40° C. under a hydrogen pressure of 5 to 25 bars, measured at 20° C., and in an alcohol (e.g. ethanol) when it is desired to obtain a compound of general formula I wherein the pair of symbols R$_1$ and the pair of symbols R$_2$ each represent a valency bond, or at a temperature between 50° and 80° C. under a hydrogen pressure of 5 to 40 bars, measured at 20° C., and in acetic acid when it is desired to obtain a compound of general formula I wherein the symbols R$_1$ and R$_2$ simultaneously represent hydrogen atoms.

The compounds of general formula II can be obtained from a compound of the general formula:

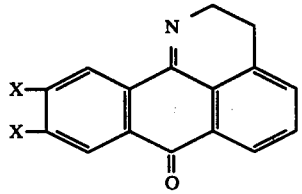

(wherein X is as hereinbefore defined) by heating in the presence of a catalyst such as palladium on charcoal. The reaction is generally carried out in an organic solvent, for example xylene, at the reflux temperature of the reaction mixture.

The compounds of general formula III can be obtained by cyclisation of a strong inorganic acid salt, e.g. hydrochloride, of a compound of the general formula:

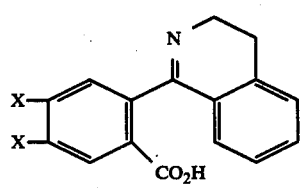

wherein X is as hereinbefore defined. The reaction is generally carried out in the presence of oleum at a temperature between 0° and 5° C.

The salts of compounds of general formula IV can be obtained from a compound of the general formula:

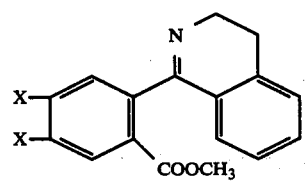

(wherein X is as hereinbefore defined) by hydrolysis in the presence of a strong inorganic acid, e.g. hydrochloric acid. The reaction is generally carried out at the reflux temperature of the reaction mixture.

The compounds of general formula V can be obtained by the action of methanol in the presence of dimethyl sulphate, or of an acid such as p-toluenesulphonic acid, on a compound of the general formula:

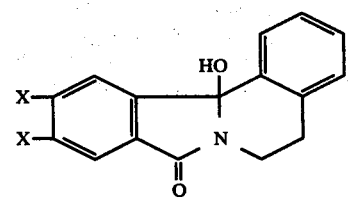

wherein X is as hereinbefore defined. The reaction is generally carried out at the reflux temperature of the reaction mixture.

The compounds of general formula VI can be obtained by oxidation with air, in the presence of a strong base, of a compound of the general formula:

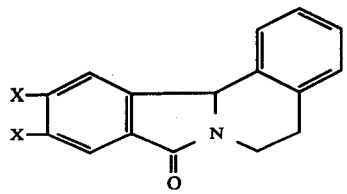

VII wherein X is as hereinbefore defined. The reaction is generally carried out in the presence of potassium hydroxide or sodium hydroxide in an alcohol, for example methanol, at the reflux temperature of the reaction mixture.

The compounds of general formula VII can be obtained by cyclisation, in an acid medium, of an isoindolinone derivative of the general formula:

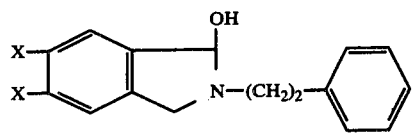

VIII wherein X is as hereinbefore defined. The reaction is generally carried out in the presence of a concentrated inorganic acid, for example hydrochloric acid, at the reflux temperature of the reaction mixture.

The compounds of general formula VIII can be obtained by partial reduction of an N-phenethylphthalimide of the general formula:

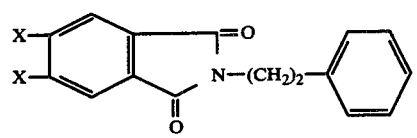

IX wherein X is as hereinbefore defined. Generally the reduction is carried out using an alkali metal borohydride in an aqueous organic medium. For example, potassium borohydride in a mixture of water, dioxan and methanol can be used.

The N-phenethylphthalimides of general formula IX can be prepared in accordance with the method described by C. Casagrande et al., Il Farmaco, Ed. Sci., 27, 445-70 (1972).

According to another feature of the invention, the compound of general formula I, wherein the symbols X, R, $R_1$ and $R_2$ simultaneously represent hydrogen atoms, is prepared from the compound of general formula I wherein R represents a hydrogen atom and the pair of symbols $R_1$ and the pair of symbols $R_2$ each represent a valency bond, that is to say from the compound of the formula:

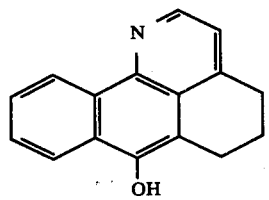

X by partial catalytic hydrogenation.

The reaction is generally effected in the presence of a hydrogenation catalyst, for example Adams platinum, at a temperature between 50° and 80° C. and under a hydrogen pressure of 5 to 40 bars, measured at 20° C., and in acetic acid.

According to still another feature of the invention, the compounds of general formula I, wherein X, $R_1$ and $R_2$ are as hereinbefore defined and R represents the carboxymethyl radical, are prepared by saponification of an ester of the general formula:

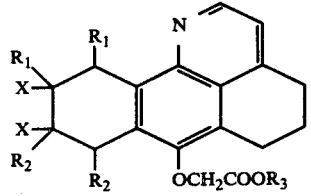

XI wherein the symbols X, $R_1$ and $R_2$ are as hereinbefore defined, and $R_3$ represents an alkyl radical containing 1 to 4 carbon atoms.

The saponification is generally carried out in the presence of a strong base, such as potassium hydroxide or sodium hydroxide, and at the reflux temperature of the reaction mixture.

The esters of general formula XI can be obtained by the action of an alkyl halogenoacetate of the general formula:

$$Y - CH_2COOR_3 \quad \text{XII}$$

(wherein Y represents a halogen atom and $R_3$ is as hereinbefore defined) on a compound of general formula I wherein R represents a hydrogen atom and X, $R_1$ and $R_2$ are as hereinbefore defined.

Generally a compound of general formula XII is reacted with an alkali metal salt, optionally prepared in situ, of a compound of general formula I, wherein R represents a hydrogen atom and X, $R_1$ and $R_2$ are as hereinbefore defined, the reaction taking place in an anhydrous organic solvent, such as dimethylformamide or tetrahydrofuran, at a temperature between −20° C. and 40° C.

The compounds of general formula I obtained by the aforedescribed processes can optionally be purified by physical methods such as chromatography or crystallisation.

The compounds of general formula I wherein X, $R_1$ and $R_2$ are as hereinbefore defined and R represents a carboxymethyl radical can be converted into metal salts or addition salts with nitrogen-containing bases by application of methods known per se. Thus, these salts can be prepared by the action of an alkali metal or an alkaline earth metal base, ammonia or an amine, on an acid product of general formula I in a suitable solvent such as an alcohol, an ether, a ketone or water; the salt formed is precipitated, if necessary after concentration of the solution, and is isolated by filtration or decantation. By the term "methods known per se" as used in this specification is meant methods heretofore used or described in the chemical literature.

The compounds of general formula I and their salts possess useful antiviral activity which acts in particular on viruses of the rhinovirus group, which viruses have the property of forming centres of necrosis in confluent cellular layers.

The compounds of general formula I induce complete inhibition, in cellular cultures of the human rhinovirus strain 2060, of the cytopathogenic effect and of the multiplication of viruses, at concentrations between 3 and 15 μg/cc (minimum inhibiting concentration) and 30 to 125 μg/cc (maximum non-cytotoxic concentration), this corresponding to an activity index of 10 to 8.3.

The compounds also exhibit an activity on three other viruses of the human respiratory system, viz. coronavirus, Coxsackie A-21 and syncytial virus of the respiratory system. Moreover, some of the compounds induce complete inhibition of the cytopathogenic effect and of the multiplication of viruses in cellular cultures of the human rhinovirus strain R 1112, at doses of about 15 μg/cc (minimum inhibiting concentration).

Their toxicity when administered orally in mice is greater than or equal to 900 mg/kg animal body weight.

Of especial interest are the compounds of general formula I wherein the pair of symbols $R_1$ and the pair of symbols $R_2$ each represent a valency bond and, when X represents a methoxy radical, R represents a hydrogen atom or, when X represents a hydrogen atom, R represents a carboxymethyl radical, or the symbols $R_1$, $R_2$, X and R each represent a hydrogen atom. Of these compounds 7-hydroxy-9,10-dimethoxy-5,6-dihydro-4H-dibenzo[de,h]quinoline exhibits a particularly marked antiviral activity.

The following Examples illustrate the invention.

EXAMPLE 1

9,10-Dimethoxy-7H-dibenzo[de,h]quinol-7-one (16.5 g) and Adams platinum (5.3 g) in suspension in ethanol (125 cc) are placed under an initial hydrogen pressure of 15 parts at 25° C. The mixture is stirred and heated at 40° C. for 12 hours. After cooling to 25° C., the catalyst is filtered off and washed four times with ethanol (total 500 cc) and then twice with methylene chloride (total 270 cc). The organic filtrates are combined and then stirred with decolourising charcoal (0.5 g), filtered and evaporated. A crystalline residue (11.5 g) is obtained which is recrystallised from acetonitrile (260 cc). After cooling for 48 hours at 5° C., the crystals are filtered off, washed with iced acetonitrile (20 cc) and dried under reduced pressure (1 mm Hg) at 60° C. A crystalline powder (7.1 g) is obtained, of which a portion (6.83 g) is recrystallised from ethanol (70 cc). After cooling for 16 hours at 5° C., the crystals are filtered off, washed twice with iced ethanol (total 20 cc) and dried under reduced pressure (1 mm Hg) at 60° C. for 12 hours. 7-Hydroxy-9,10-dimethoxy-5,6-dihydro-4H-dibenzo[de,h]quinoline (4.56 g), melting at 218° C., is thus obtained.

9,10-Dimethoxy-7H-dibenzo[de,h]quinol-7-one can be obtained in the following way:

9,10-Dimethoxy-2,3-dihydro-7H-dibenzo[de,h]quinol-7-one (2.93 g) and palladium on charcoal (8.2 g; containing 3.1% of palladium) are suspended in xylene (488 cc). and the suspension is heated under reflux for three hours. After filtration whilst hot and concentration, 9,10-dimethoxy-7H-dibenzo[de,h]quinol-7-one (2.65 g), melting at 250° C., is obtained.

9,10-Dimethoxy-2,3-dihydro-7H-dibenzo[de,h]quinol-7-one can be obtained in the following way:

1-(2-Carboxy-4,5-dimethoxyphenyl)-3,4-dihydroisoquinoline hydrochloride (40 g) is added in small fractions to sulphuric acid (d = 1.88; 300 cc) containing 20% by weight of sulphur trioxide, the temperature being maintained between 0° and 5° C. The reaction mixture is maintained for a further 16 hours at this temperature after the end of the addition, and then it is poured with care onto crushed ice (3 kg) and treated with concentrated ammonia (d = 0.92; 1500 cc) care being taken that the temperature of the reaction mixture does not exceed 20° C. The resulting precipitate is filtered off, washed three times with water (total 900 cc) and dried in air. A crude product (24.15 g), melting at 208°–210° C., is obtained.

A portion (20 g) of the product thus obtained is dissolved in boiling 1,2-dichloroethane (400 cc). The resulting solution is filtered, whilst hot, through alumina (20 g) which is then washed twice with 1,2-dichloroethane (total 20 cc). The filtrates are combined and cooled for 16 hours at 5° C. The crystals which appear are filtered off, washed three times with iced 1,2-dichloroethane (total 40 cc) and dried under reduced pressure (1 mm Hg at 60° C. for 8 hours). 9,10-Dimethoxy-2,3-dihydro-7H-dibenzo[de,h]quinol-7-one (13 g), melting at 228° C., is thus obtained.

1-(2-Carboxy-4,5-dimethoxyphenyl)-3,4-dihydroisoquinoline hydrochloride can be obtained in the following way:

1-(4,5-Dimethoxy-2-methoxycarbonylphenyl)-3,4-dihydroisoquinoline (110.5 g) is suspended in N hydrochloric acid (1000 cc). Thereafter, the suspension is heated under reflux for three and a half hours and then cooled to about 0° C. and the precipitate which appears is filtered off. A crude product (62.8 g), melting at 190° C., is thus obtained.

A portion (19 g) of the product thus obtained is dissolved in ethanol (400 cc) and treated with decolourising charcoal (2 g). After filtration and the addition of diethyl ether (3500 cc), the resulting precipitate is filtered off, washed with iced diethyl ether (30 cc) and dried under reduced pressure (1 mm Hg) at 60° C. for 16 hours. 1-(2-Carboxy-4,5-dimethoxyphenyl)-3,4-dihydroisoquinoline hydrochloride (15.6 g), melting at 193°–194° C., is thus obtained.

1-(4,5-Dimethoxy-2-methoxycarbonylphenyl)-3,4-dihydroisoquinoline can be obtained in the following way:

Dimethyl sulphate (48 cc) is added to a suspension of 12b-hydroxy-10,11-dimethoxy-5,6,8,12b-tetrahydroisoindolo[1,2-a]isoquinol-8-one (80.65 g) in methanol (563 cc) and the reaction mixture is heated under reflux for 6 hours. After concentration to 100 cc and the successive addition of water (300 cc) and then of 10N sodium hydroxide (70 cc), the mixture is extracted three times with ethyl acetate (total 400 cc). The combined organic solutions are washed three times with distilled water (total 400 cc), dried over anhydrous sodium sulphate, treated with decolourising charcoal (1 g), filtered and evaporated. 1-(4,5-Dimethoxy-2-methoxycarbonylphenyl)-3,4-dihydroisoquinoline (67.8 g), melting at 133° C., is thus obtained.

12b-Hydroxy-10,11-dimethoxy-5,6,8,12b-tetrahydroisoindolo[1,2-a]isoquinol-8-one can be obtained in the following way:

10,11-Dimethoxy-5,6,8,12b-tetrahydro-isoindolo[1,2-a]isoquinoline (109.65 g) and potassium hydroxide in pellet form (23.2 g) are dissolved in methanol (1100 cc). Air is bubbled into the reaction mixture, which is heated under reflux for 3 hours and then maintained at 25° C. for 48 hours. After concentration to 500 cc, the addition of distilled water (5000 cc) and stirring for 2 hours, a precipitate appears which is filtered off, washed three times with distilled water (total 500 cc) and dried under reduced pressure (20 mm Hg) at 40° C. A crude product (104.65 g), melting at 219° C., is obtained. A solution of a portion of this product (30 g) in dimethylformamide (200 cc) at 120° C. is treated with decolourising charcoal (1 g), filtered whilst hot, and cooled at about 5° C. for 16 hours. The resulting crystals are filtered off, washed three times with diisopropyl ether (total 30 cc) and dried under reduced pressure (1 mm Hg) at 60° C. for 6 hours. 12b-Hydroxy-10,11-dimethoxy-5,6,8,12b-tetrahydro-isoindolo[1,2-a]isoquinol-8-one (16.70 g), melting at 220° C., is thus obtained.

10,11-Dimethoxy-5,6,8,12b-tetrahydro-isoindolo-[1,2-a]isoquinoline can be obtained in the following way:

3-Hydroxy-2-Phenethyl-5,6-dimethoxy-2,3-dihydro-1H-isoindol-1-one (23 g) is suspended in a concentrated hydrochloric acid (d = 1.18; 220 cc). The suspension is heated under reflux for 1 hour. After the addition of distilled water (1100 cc), the mixture is maintained at 60° C. for 10 minutes and then cooled at 10° C. for 2 hours. The resulting crystals are filtered off, washed three times, until neutral, with distilled water (total 150 cc) and dried under reduced pressure (20 mm Hg) at 25° C. A product (16.85 g), melting at 184° C., is thus obtained which is purified by chromatography over silica gel.

Elution is carried out successively with cyclohexane (80 cc), then with mixtures of cyclohexane and ethyl acetate (7 fractions of 100 cc) containing increasing proportions of ethyl acetate, and finally with an ethyl acetate fraction (650 cc). The eluates corresponding to these fractions are discarded. Elution is then carried out with ethyl acetate (total 6000 cc). The corresponding eluate is collected and concentrated to dryness. A product (13.45 g), melting at 185° C., is obtained which is recrystallised from ethanol (320 cc). After sixteen hours at 5° C., the crystals are filtered off, washed three times with iced ethanol (total 30 cc) and dried under reduced pressure (1 mm Hg at 60° C. for 7 hours). 10,11-Dimethoxy-5,6,8,12b-tetrahydro-isoindolo[1,2-a]isoquinoline (10.95 g), melting at 186° C., is thus obtained.

3-Hydroxy-2-phenethyl-5,6-dimethoxy-2,3-dihydro-1H-isoindol-1-one can be obtained in the following way:

Potassium borohydride (4.87 g) dissolved in distilled water (58.7 cc) is added to 4,5-dimethoxy-N-phenethyl phthalimide (28 g) suspended in a mixture (180 cc) consisting of equal volumes of dioxan and methanol. The reaction mixture is heated under reflux for 2 hours and then concentrated to a volume of 60 cc and distilled water (450 cc) is added. After cooling, the resulting precipitate is filtered off, washed three times with distilled water (total 1000 cc) and dried under reduced pressure (20 mm Hg) at 25° C. 3-Hydroxy-2-phenethyl-5,6-dimethoxy-2,3-dihydro-1H-isoindol-1-one (27.3 g), melting at 130° C., is thus obtained.

4,5-Dimethoxy-N-phenethyl phthalimide, m.p. 185° C., can be prepared according to the method described by C. Casagrande, A. Galli, R. Ferrini and G. Miragoli, Il Farmaco, Ed. Sci. 27, 445-70 (1972).

EXAMPLE 2

7H-Dibenzo[de,h]quinol-7-one (17.4 g) and Adams platinum (5.8 g) suspended in ethanol (394 cc) are placed under an initial hydrogen pressure of 10 bars at 25° C. The mixture is stirred for 23 hours at 25° C. The catalyst is filtered off and washed four times with dimethylformamide (total 1000 cc). The combined organic solutions are evaporated to dryness. The residue (22.1 g) is stirred for one hour with distilled water (500 cc) and then the precipitate is filtered off, washed twice, successively, with ethanol (total of 20 cc) and then dried under reduced pressure (20 mm Hg) at 20° C. A crude product (15.8 g) is obtained which is recrystallised from a mixture (300 cc) of equal parts of ethanol and dimethylformamide. After cooling for 20 hours at about 5° C., the crystals are filtered off, washed three times with diethyl ether (total 60 cc) and dried under reduced pressure (1 mm Hg) at 100° C. The product obtained (12.1 g) is recrystallised a second time from butyl acetate (410 cc). After cooling for 16 hours at 5° C., the crystals are filtered off, washed twice with ethyl acetate (total 20 cc) and dried under reduced pressure (1 mm Hg) at 100° C. for 8 hours. 7-Hydroxy-5,6-dihydro-4H-dibenzo[de,h]quinoline (11.3 g), melting at 260° C., is thus obtained.

7H-Dibenzo[de,h]quinol-7-one (m.p. 185° C.) employed as starting material can be prepared according to the method described in German Pat. No. 614,196.

EXAMPLE 3

7-Hydroxy-5,6-dihydro-4H-dibenzo[de,h]quinoline (16.4 g) and Adams platinum (2.78 g) suspended in acetic acid (400 cc) are placed under an initial hydrogen pressure of 25 bars at 25° C. The mixture is stirred and heated at 65° C. for 24 hours. After cooling to 25° C., the catalyst is filtered off and washed three times with acetic acid (total 200 cc). The combined organic filtrates are evaporated to dryness. The residue is taken up in water (500 cc) and the mixture is neutralised by the addition of a 10% (w/v) aqueous sodium bicarbonate solution (50 cc). The precipitate is filtered off, washed three times with distilled water (total 600 cc) and dried under reduced pressure. The crystalline product thus obtained (17 g) is combined with a portion (7.4 g) of product prepared in the same way, the whole is recrystallised from butyl acetate (550 cc). After cooling for 48 hours at about 5° C., the resulting crystals are filtered off, washed twice with diethyl ether (total 75 cc) and dried under reduced pressure (1 mm Hg) at 100° C. The product obtained (18.5 g) is recrystallised a second time from propanol (360 cc). After cooling for 48 hours at about 5° C., the crystals are filtered off, washed twice with diethyl ether (total 75 cc) and dried under reduced pressure (1 mm Hg) at 100° C. for 4 hours. 7-Hydroxy-5,6,8,9,10,11-hexahydro-4H-dibenzo[de,h]-quinoline (14.5 g), melting at 224° C., is thus obtained.

EXAMPLE 4

7H-Dibenzo[de,h]quinol-7-one (48.4 g) and Adams platinum (16 g) suspended in acetic acid (800 cc) are placed under an initial hydrogen pressure of 30 bars at 25° C. The mixture is stirred and heated at 65° C. for 17 hours. After cooling to about 25° C., the catalyst is filtered off and washed twice with acetic acid (total 150 cc). The combined organic filtrates are evaporated to dryness. The residue is taken up in water (1000 cc) and adjusted to pH 9 by the addition of 5N sodium hydroxide. The resulting precipitate is filtered off, washed twice with distilled water (total 2000 cc) and four times with ethanol (total 100 cc) and then dried under reduced pressure (20 mm Hg) at 20° C. Crude 7-hydroxy-5,6,8,9,10,11-hexahydro-4H-dibenzo[de,h]quinoline (46.1 g), melting at 224° C., is thus obtained, which is recrystallised successively from butyl acetate and from propanol as described in Example 3.

EXAMPLE 5

Ethyl (5,6-dihydro-4H-dibenzo[de,h]quinol-7-yloxy)acetate (14.5 g) is suspended in 2N sodium hydroxide (580 cc). The suspension obtained is heated under reflux for 1 hour and 50 minutes and then cooled. The resulting crystals are filtered off and dissolved in acetic acid (250 cc). The solution obtained is evaporated to dryness. The residue is taken up in a mixture of distilled water (200 cc) and diethyl ether (50 cc). After stirring for 15 minutes the precipitate is filtered off, washed 10 times with distilled water (total 500 cc) and twice with diethyl ether (total 25 cc), and then dried under reduced pressure (20 mm Hg) at 20° C. A product (13.15 g) is obtained which is recrystallised from a mixture of ethyl acetate (1000 cc) and isopropanol (535 cc). After cooling for 48 hours at about 5° C., the crystals are filtered off, washed three times with iced ethyl acetate (total 50 cc) and dried under reduced pressure (20 mm Hg) at 20° C. The crystalline product thus obtained (7.6 g) is combined with the product obtained (3.8 g) by concentration of the mother liquors, and the whole is recrystallised a second time from acetic acid (60 cc). After cooling for 16 hours at about 20° C., the precipitate is filtered off, washed four times with distilled water (total 200 cc) and twice with iced ethyl acetate (total 50 cc) and dried under reduced pressure (1 mm Hg) at 60° C. for 11 hours. (5,6-Dihydro-4H-dibenzo[de,h]quinol-7-yloxy)acetic acid (8.9 g), melting at 228° C., is thus obtained.

Ethyl (5,6-dihydro-4H-dibenzo[de,h]quinol-7-yloxy)acetate employed as starting material can be obtained in the following way:

7-Hydroxy-5,6-dihydro-4H-dibenzo[de,h]quinoline (27 g) [prepared as described in Example 2] is added to a suspension of sodium hydride (50% dispersion in mineral oil; (5.75 g) in anhydrous dimethylformamide (520 cc) and then, after stirring for 4 hours, ethyl bromoacetate (21.3 g) in solution in anhydrous dimethylformamide (20 cc) is added. The reaction mixture is maintained for 22 and a half hours at about 20° C., is distilled water (10 cc) is added, the mixture is concentrated to a volume of 400 cc, distilled water (4600 cc) is added and the mixture is extracted eight times with diethyl ether (total 3500 cc). The combined organic solutions are washed four times with distilled water (total 4000 cc), dried over anhydrous sodium sulphate, treated with decolourising charcoal (5 g), filtered and evaporated to dryness. The residue is dried by azeotropic distillation with methylene chloride (150 cc) and then crystallised from ethanol (16 cc). After cooling for 21 hours at about 5° C., the resulting crystals are filtered off, washed twice with ethanol (total 18 cc), which has been cooled to −20° C., and dried under reduced pressure (20 mm Hg) at 20° C. Ethyl (5,6-dihydro-4H-dibenzo[de,h]quinol-7-yloxy)acetate (16.95 g), melting at 70° C., is thus obtained.

The present invention includes within its scope pharmaceutical compositions comprising, as active ingredient, at least one of the compounds of general formula I, or — in the case of those compounds wherein R represents a carboxymethyl radical — a pharmaceutically acceptable salt thereof, in association with a pharmaceutical carrier or coating. The invention includes especially such preparations made up for oral, intranasal or rectal administration.

Solid compositions for oral administration include tablets, pills, powders and granules. In such solid compositions the active compound is admixed with one or more inert diluents, such as sucrose, lactose or starch. The compositions may also comprise, as is normal practice, substances other than inert diluents, for example a lubricating agent such as magnesium stearate. Liquid compositions for oral administration include pharmaceutically acceptable emulsions, solutions, suspensions, syrups and elixirs containing inert diluents commonly used in the art such as water or liquid paraffin. These compositions can also contain substances other than the diluents, for example wetting agents, sweetening agents or aromatizing agents.

The compositions for intranasal administration can be aqueous or non-aqueous sterile solutions, suspensions or emulsions. Propylene glycol, a polyethylene glycol, vegetable oils, in particular olive oil, and organic esters, for example ethyl oleate, can be used as the solvent or vehicle for the compound. These compositions can also contain adjuvants, in particular wetting agents, emulsifiers and dispersing agents. Sterilisation can be effected in various ways, for example with the aid of a bacteria-retaining filter, by incorporation of sterilising agents in the composition, by irradiation or by heating. They can also be prepared in the form of sterile solid compositions which can be dissolved, at the time of use, in sterile water or any other suitable sterile medium.

The compositions for rectal administration are suppositories which contain, in addition to the active compound, excipients such as cacao butter or a suitable wax base.

The compositions according to the invention are particularly useful for their anti-viral action. They are particularly indicated for the treatment of viral infections of the respiratory passages.

In human therapy, the doses to be used depend on the therapeutic effect desired, the method of administration and the duration of the treatment; administered orally, they can generally be between 1 and 2 g of active compound per day, in the case of an adult, and they can attain 200 mg per day, administered nasally (as drops or as sprays).

In general the physician will determine the posology considered appropriate, taking into account the age and weight and other factors intrinsic to the patient being treated.

The following Examples illustrate pharmaceutical compositions according to the invention.

EXAMPLE 6

A 1% (w/v) solution in oil, for intranasal administration, is obtained by dissolving 7-hydroxy-9,10-dimethoxy-5,6-dihydro-4H-dibenzo[de,h]quinoline (1 g) in olive oil (100 cc) at 40°–50° C. and filtering the solution obtained through a Millipore filter. For use, the solution is applied to the nasal mucous membrane using a dropper.

EXAMPLE 7

A 1% (w/v) solution of 7-hydroxy-9,10-dimethoxy-5,6-dihydro-4H-dibenzo[de,h]quinoline is prepared for intranasal administration by dissolving the compound (1 g) in propylene glycol (90 cc) and making the solution up to 100 cc with distilled water. The solution is sterilised by passing through a Millipore filter. For use, the resulting solution is applied to the nasal mucous membrane using a dropper.

We claim:
1. A dibenzo[de,h]quinoline of the formula:

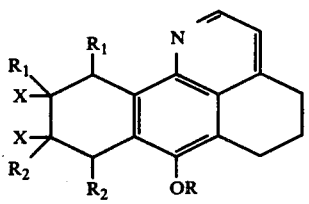

wherein the symbols X each represent hydrogen or methoxy, R represents hydrogen or carboxymethyl, the symbols $R_1$ each represent hydrogen or together represent a valency bond, the pair of symbols $R_2$ have the same significance as the pair of symbols $R_1$, and, when the symbols $R_1$ and $R_2$ represent hydrogen the symbols X also represent hydrogen, and, when R is carboxymethyl, a pharmaceutically acceptable salt thereof.

2. A dibenzo[de,h]quinoline according to claim 1 wherein the pair of symbols $R_1$ and the pair of symbols $R_2$ each represent a valency bond and, when X represents methoxy, R represents hydrogen or, when X represents hydrogen, R represents carboxymethyl, or the symbols $R_1$, $R_2$, X and R each represent hydrogen.

3. The dibenzo[de,h]quinoline according to claim 1 which is 7-hydroxy-9,10-dimethoxy-5,6-dihydro-4H-dibenzo[de,h]quinoline.

4. The dibenzo[de,h]quinoline according to claim 1 which is 7-hydroxy-5,6-dihydro-4H-dibenzo[de,h]quinoline.

5. The dibenzo[de,h]quinoline according to claim 1 which is 7-hydroxy-5,6,8,9,10,11-hexahydro-4H-dibenzo[de,h]quinoline.

6. The dibenzo[de,h]quinoline according to claim 1 which is (5,6-dihydro-4H-dibenzo-[de,h]quinol-7-yloxy)acetic acid and its pharmaceutically acceptable salts.

7. A pharmaceutically acceptable alkali metal, alkaline earth metal, ammonium, or amine salt of a dibenzo[de,h]quinoline as claimed in claim 1 wherein R represents carboxymethyl.

8. An anti-viral pharmaceutical composition which comprises a dibenzo[de,h]quinoline as claimed in claim 1, or, when R is carboxymethyl, a pharmaceutically acceptable salt thereof, in association with a pharmaceutically acceptable carrier.

* * * * *